US008586334B2

(12) United States Patent
Nakai et al.

(10) Patent No.: US 8,586,334 B2
(45) Date of Patent: Nov. 19, 2013

(54) METHOD FOR PRODUCING SUBSTANCE UTILIZING MICROORGANISM

(75) Inventors: Yuta Nakai, Kawsaki (JP); Kazuo Nakanishi, Kawasaki (JP); Yoshio Kawahara, Kawasaki (JP); Hisao Ito, Kawasaki (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1464 days.

(21) Appl. No.: 09/897,988

(22) Filed: Jul. 5, 2001

(65) Prior Publication Data

US 2002/0160461 A1 Oct. 31, 2002

(30) Foreign Application Priority Data

Jul. 5, 2000 (JP) ................................ 2000-204252

(51) Int. Cl.
*C12P 13/04* (2006.01)
*C12P 13/08* (2006.01)
*C12N 1/21* (2006.01)
*C12N 9/00* (2006.01)

(52) U.S. Cl.
USPC ........ 435/106; 435/108; 435/252.33; 435/183

(58) Field of Classification Search
USPC ............ 435/252.33, 108, 110, 116, 106, 115, 435/93.2, 252.1, 849
See application file for complete search history.

(56) References Cited

U.S. PATENT DOCUMENTS

| 4,104,124 | A | * | 8/1978 | Srinivasan et al. | ............. | 435/110 |
| 5,175,108 | A | * | 12/1992 | Bachmann et al. | ....... | 435/252.32 |
| 5,830,716 | A | * | 11/1998 | Kojima et al. | ................. | 435/106 |
| 2002/0106800 | A1* | | 8/2002 | Liaw et al. | ..................... | 435/488 |
| 2005/0221455 | A1* | | 10/2005 | McFarlan et al. | ............. | 435/121 |

FOREIGN PATENT DOCUMENTS

| EP | 0 967 282 | 12/1999 |
| WO | WO 99/46363 | 9/1999 |

OTHER PUBLICATIONS

JE Bailey, Science, "Toward a Science of Metabolic Engineering," Jun. 1991, vol. 252, pp. 1668-1675.*
DT Ciccognani et al., FEMS Microbiology Letters,"Carbon monoxide-binding properties of the cytochrome bo quinol oxidase complex in *Escherichia coli* are changed by copper deficiency in continuous culture," 1992, 94, 1-6.*
Neijssel and de Mattos. The energetics of bacterial growth: a reassessment. Molecular Microbiology. (1994) 13(2), pp. 179-182.*
Parekh et al. Improvement of microbial strains and fermentation processes. Appl Microbiol. Biotechnol. (2000) 54, pp. 287-301.*
Spehr et al, Overexpression of the *Escherichia coli* nuo-Operon and Isoaltion of the overporduced NADH:Ubiquinone Oxidoreductase (Complex I), Biochemistry, 1999, vol. 38, pp. 16261-16267.*

Bott and Niebisch, The respiratory chain of *Corynebacterium glutamicum*, J Biotechnology, 2003, vol. 104, pp. 129-153.*
Castresana, J. Comparative genomics and Bioenergetics, Biochimica et Biophysica Acta, 2001, 1506,pp. 147-162.*
Castresana and Saraste, Evolution of energetic metabolism: the respiration-early hypothesis, TIBS, 1995, vol. 20, pp. 443-448.*
Kusomoto et al, Menaquinol oxidase activity and primary structure of cytochrome bd from the amino-acid fermenting bacterium *Corynebacterium glutamicum*,Arch Microbiol (2000) 173 :390-397.*
Calhoun et al, Energetic efficiency of *Escherichia coli*: effects of mutations in components of the aerobic respiratory chain, J Bacteriol. May 1993; 175(10): 3020-3025.*
Melissa W. Calhoun, et al., Journal of Bacteriology, vol. 175, No. 10, pp. 3020-3025, "Energetic Efficiency of *Escherichia Coli*: Effects of Mutations in Components of the Aerobic Respiratory Chain", May 1993.
Nobuhito Sone, et al., Journal of Biochemistry (Tokyo), vol. 127, No. 4, pp. 551-557, "Energy-Yielding Properties of *SOXB*-Type Cytochrome $BO_3$ Terminal Oxidase: Analyses Involving *Bacillus Stearothermophilus* K1041 and Its Mutant Strains[1]", Apr. 2000.
Nobuhito Sone, et al., Journal of Bioscience and Bioengineering, vol. 87, No. 4, pp. 495-499, "Direct Correlationship Between Proton Translocation and Growth Yield: An Analysis of the Respiratory Chain of *Bacillus Stearothermophilus*", Apr. 1999.
Kuniichiro Kusumoto, et al., vol. 173, No. 5-6, pp. 390-397, "Menaquinol Oxidase Activity and Primary Structure of Cytochrome *BD*From the Amino-Acid Fermenting Bacterium *Corynebacterium glutamicum*", May 2000.
J. Bongaerts, et al., Molecular Microbiology, vol. 16, No. 3, pp. 521-534, "Transcriptional Regulation of the Proton Translocating NADH Dehydrogenase Genes (*nuoA-N*) of *Escherichia coli* by Electron Acceptors, Electron Donors and Gene Regulators", 1995.
M. W. Calhoun, et al., Journal of Bacteriology, vol. 175, No. 10, pp. 3020-3025, "Energetic Efficiency of *Escherichia coli*: Effects of Mutations in Components of the Aerobic Respiratory Chain", May 1993.

(Continued)

*Primary Examiner* — Maria Marvich
(74) *Attorney, Agent, or Firm* — Shelly Guest Cermak; Cermak Nakajima LLP (57) ABSTRACT

In a method for producing a target substance utilizing a microorganism comprising culturing the microorganism in a medium to produce and cause accumulation of the target substance in the medium and collecting the target substance, there is used, as the microorganism, a mutant strain or a genetic recombinant strain constructed from a parent strain of the microorganism having a respiratory chain pathway of high energy efficiency and a respiratory chain pathway of low energy efficiency as respiratory chain pathways, and having either one or both of the following characteristics:

(A) the respiratory chain pathway of high energy efficiency is enhanced, (B) the respiratory chain pathway of low energy efficiency is deficient.

6 Claims, 2 Drawing Sheets

(56) References Cited

OTHER PUBLICATIONS

V. Chepuri, et al., The Journal of Biological Chemistry, vol. 265, No. 19, pp. 11185-11192, "The Sequence of the *CYO* Operon Indicates Substantial Structural Similarities Between the Cytochrome O Ubiquinol Oxidase of *Escherichia coli* and the $AA_3$-Type Family of Cytochrome C Oxidases", Jul. 5, 1990.

J. Green, et al., Molecular Microbiology, vol. 12, No. 3, pp. 433-444, "Regulation of Trnscription at the *NDH* Promoter of *Escherichia coli* by FNR and Novel Factors", 1994.

J. Minagawa, et al., The Journal of Biological Chemistry, vol. 265, No. 19, pp. 11198-11203, "Transcriptional Regulation of the Cytochrome $B_{562}$-O Complex in *Escherichia coli*", Jul. 5,1990.

Ching-Ping Tseng, et al., Journal of Bacteriology, vol. 178, No. 4, pp. 1094-1098, "Effect of Microaerophilic Cell Growth Conditions on Expression of the Aerobic (*cyoABCDE* and *cydAB*) and Anaerobic (*narGHJI, frdABCD*, and *dmsABC*) Respiratory Pathway Genes in *Escherichia coli*", Feb. 1996.

I. G. Young, et al., Eur. J. Biochem., vol. 116, pp. 165-170, "Nucleotide Sequence Coding for the Respiratory NADH Dehydrogenase of *Escherichia coli*", 1981.

Lena Winstedt, et al., Cytochrome *bd* Biosynthesis in *Bacillus subtilis*: Characterization of the *cydABCD* Operon, Journal of Bacteriology, vol. 180, No. 24, Dec. 1998. pp. 6571-6580.

Margarida Santana, et al.. Molecular Cloning, Sequencing, and Physiological Characterization of the *auox* Operon from *Bacillus subtilis* Encoding the $aa_3$-600 Quinol Oxidase, The Journal of Biological Chemistry, vol. 267, No. 15, May Issue, 1992, pp. 10225-10231.

Junshi Sakamoto, et al., Gene Structure and Quinol Oxidase Activity of a Cytochrome *bd*-type Oxidase from *Bacillus sterothermophilus*, Biochimica et Biophysica Acta, 1411, 1999, pp. 147-158.

Alessandro Giuffre, et al., Electron Transfer Kinetics of $caa_3$ Oxidase from *Bacilllus stearothermophilus* a Hypothesis of Thermophilicity, Biophysical Journal, vol. 76, Jan. 1999. pages 438-442.

Junshi Sakamoto, et al., Cytochrome c Oxidase Contains an Extra Charged Amino Acid Cluster in a New Type of Respiratoroy Chain in the Amino-acid-producing Gram-positive Bacterium *Corynebacterium glutamicum*, Microbiologoy, 2001, 147, 2865-2871.

Collection of Summaries of Lectures made at the Meeting of Japan Bioengineering Association, Sep. 15, 1995, p. 105, with English translation thereof.

\* cited by examiner

SEQUENCE LISTING

<160> NUMBER OF SEQ ID NOS: 2

<210> SEQ ID NO 1
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
cgatggaagc ttccgcgatt atggg         25

<210> SEQ ID NO 2
<211> LENGTH: 27
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
aagcgcggaa ttcgtccttc aatcatc       27

METHOD FOR PRODUCING SUBSTANCE UTILIZING MICROORGANISM

BACKGROUND OF THE INVENTION

1. Field of the Invention

The present invention relates to a method which uses a microorganism for producing a substance. In the present invention, the microorganism is typically a bacteria belonging to the genus *Escherichia*, or coryneform bacteria, which are conventionally used for production of substances. The substance to be produced may be selected from those conventionally produced by using microorganisms, for example, L-amino acids, nucleic acids, antibiotics, vitamins, growth factors, physiologically active substances, and so forth. The present invention discloses means for improving production of final target substances in methods using microorganisms for producing substances.

2. Description of the Related Art

Many of organisms acquire energy required for survival and function by respiration. In the respiration of microorganisms, the function of various enzyme complexes is generally dependent on the species or growth environment, and energy acquisition efficiency also can vary significantly. Carbohydrates, proteins and aliphatic acids are converted into acetyl-CoA by the glycolysis, β-oxidation, and so forth, and decomposed in the citric acid cycle. Then, the energy preserved in the form of NADH is used for proton excretion from microbial cells with the aid of NADH dehydrogenase (NDH), and an electron transfer system consisting of oxidoreductases, and thereby a proton concentration gradient, is formed between the inside and outside of the cytoplasmic membrane. This proton concentration gradient is the driving force of adenosine triphosphate (ATP) synthesis. At this time, pathways of electron transfer include pathways showing high and low proton excretion ability, depending on the combination of NDH and oxidoreductases. It is thought that a pathway of high proton excretion ability shows high energy efficiency and a pathway of low proton excretion ability shows low energy efficiency. Thus, one kind of microorganism simultaneously contains a plurality of respiratory chain electron transfer pathways in parallel, and those pathways include those of high energy efficiency and low energy efficiency.

Two kinds each of NDHs and terminal oxidases exist in the respiratory chain of *Escherichia coli* under aerobic conditions. That is, NDH-1, encoded by the nuo operon, is known to have high energy efficiency, and NDH-II, encoded by ndh, is known to have low energy efficiency. Furthermore, cytochrome bo-type oxidase, encoded by the cyoABCD operon, and classified as a SoxM type (Castresana, J. and Saraste, M., *Trends in Biochem. Sci*, 20, 443-448 (1995)) is known to show high energy efficiency, and cytochrome bd-type oxidase, encoded by cydAB, is known to show low energy efficiency. Although it is known that the levels of expression of these respiratory chain enzymes vary in response to their growth environment (Minagawa et al., *The Journal of Biological Chemistry*, 265:11198-11203 (1990); Tseng et al., *Journal of Bacteriology*, 178:1094-1098 (1996); Green et al., *Molecular Microbiology*, 12:433-444 (1994); Bongaerts et al., *Molecular Microbiology*, 16:521-534 (1995)), much is unknown about the physiological meaning of their expression patterns.

Furthermore, *Corynebacterium glutamicum* contains a cytochrome bc1 complex and at least two kinds of terminal oxidases, SoxM type oxidase and cytochrome bd type oxidase (The Second Symposium Concerning Metabolic Engineering, Lecture Abstracts, 1999). This shows that there are two kinds of electron transfer pathways from a quinone pool to an oxygen molecule and include a pathway utilizing cytochrome bc1 complex and SoxM type oxidase, and a pathway utilizing only the cytochrome bd type oxidase. It is thought that the former is an electron transfer pathway of high energy efficiency in which the proton transfer value for transfer of one electron is high, and the latter is an electron transfer pathway of low energy efficiency in which proton transfer value for transfer of one electron is low.

As for the terminal oxidase of *E. coli*, in a comparison of growth yields in aerobic cultures of a mutant strain having only the cytochrome bo-type oxidase, a mutant strain having only the cytochrome bd-type oxidase, and a wild-type strain having both, the growth yield will be the lowest in the mutant strain having only the cytochrome bd-type oxidase, and it depends on the kind and energy acquisition efficiency of terminal oxidase (Annual Meeting of the Society for fermentation and Bioengineering Japan, 1995, Lecture Abstracts, No. 357).

Furthermore, the energy efficiency of deficient mutants of some respiratory chain enzymes has been reported (Calhoun et al., *Journal of Bacteriology*, 17.5:3020-3925 (1993)).

However, there have been no reports concerning a change in energy efficiency by amplification of a respiratory chain gene providing high efficiency such as those for NDH-I and SoxM type oxidase, and an attempt to utilize such for production of substances has also not been reported. Furthermore, no attempts have been made to delete a respiratory chain enzyme of low efficiency such as NDH-II and cytochrome bd-type oxidase for production of substances.

SUMMARY OF THE INVENTION

Energy is required for biosynthesis of substances such as L-amino acids and nucleic acids in living bodies. Most energy used consists of the reducing powers of NADH, NADPH, and so forth, and energy preserved as ATP. Therefore, the inventors of the present invention conceived that, if the energy supply utilized in the production of target substances was increased in methods for producing target substances utilizing microorganisms, production of the target substances would be improved. Based on such a concept, an object of the present invention is to construct a microorganism showing improved energy efficiency and provide a method for producing a target substance by utilizing this method.

The inventors of the present invention conceived that a microorganism having an increased energy supply could be constructed by enhancing a respiratory chain pathway having high energy acquisition efficiency or making deficient a respiratory chain pathway showing low energy acquisition efficiency. Specifically in *E. coli*, strains considered to have improved energy efficiency were prepared by amplifying a gene coding for cytochrome bo-type oxidase, a respiratory chain enzyme of high energy efficiency, or deleting a gene coding for NDH-II, a respiratory chain enzyme of low energy efficiency. Then, L-amino acid production was performed using these strains and it was found that the L-amino acid production was improved in strains whose energy efficiency was improved. Thus, the present invention was accomplished.

That is, the present invention provides the following.

(1) A method for producing a target substance utilizing a microorganism comprising culturing the microorganism in a medium to produce and cause accumulation of the target substance in the medium and collecting the target substance, wherein the microorganism is constructed from a parent strain of the microorganism having a respiratory chain pathway of high energy efficiency and a respiratory chain pathway of low energy efficiency as respiratory chain pathways, and the microorganism is a mutant strain or a genetic recombinant strain having either one or both of the following characteristics:

(A) The respiratory chain pathway of high energy efficiency is enhanced, (B) The respiratory chain pathway of low energy efficiency is deficient.

(2) The method for producing a target substance according to (1), wherein the respiratory chain pathway of high energy efficiency is enhanced by increasing a copy number of a gene coding for an enzyme involved in the respiratory chain or modification of an expression regulatory sequence of the gene.

(3) The method for producing a target substance according to (1) or (2), wherein the respiratory chain pathway of low energy efficiency is made deficient by disruption of a gene coding for an enzyme involved in the respiratory chain.

(4) The method for producing a target substance according to any one of (1) to (3), wherein the respiratory chain enzymes having high energy efficiency include SoxM type oxidase, bc1 complex, NDH-1, or combinations thereof.

(5) The method for producing a target substance according to any one of (1) to (4), wherein the respiratory chain enzymes having low energy efficiency include cytochrome bd type oxidase, NDH-II, or both.

(6) The method for producing a target substance according to any one of (1) to (5), wherein SoxM type oxidase activity is enhanced and NDH-II is made deficient in the microorganism.

(7) The method for producing a target substance according to any one of Claims (1) to (6), wherein the SoxM type oxidase is cytochrome bo-type oxidase.

(8) The method for producing a target substance according to any one of (1) to (7), wherein the microorganism is a bacterium belonging to the genus *Escherichia or coryneform* bacterium.

(9) The method for producing a target substance according to any one of (1) to (8), wherein the target substance is an L-amino acid or nucleic acid.

According to the present invention, production of the target substance in a method utilizing a microorganism comprising culturing the microorganism in a medium to produce and cause accumulation of the target substance in the medium and collecting the target substance can be improved based on a novel principle.

DETAILED DESCRIPTION OF THE INVENTION

Hereinafter, the present invention will be explained in detail.

The substance produced by the production method of the present invention is not particularly limited so long as it is a substance that can be produced by a microorganism. Examples thereof include L-amino acids such as L-threonine, L-lysine, L-glutamic acid, L-leucine, L-isoleucine, L-valine, and L-phenylalanine; nucleic acids such as guanylic acid and inosinic acid; vitamins; antibiotics; growth factors; physiologically active substances; and so forth.

The microorganism of the present invention is a microorganism having an ability to produce a target substance as described above, constructed from a parent strain of a microorganism having respiratory chain pathways of high and low energy efficiencies, and having either one or both of the following characteristics:

(A) the respiratory chain pathway of high energy efficiency is enhanced, (B) the respiratory chain pathway of low energy efficiency is deficient.

In general, microorganisms including *E. coli* and coryneform bacteria contain a plurality of respiratory chain electron transfer pathways which function in parallel. These pathways include those which have high and low proton transfer value per electron. In *E. coli*, for example, NDHI and NDHII as NADH dehydrogenase act as electron donors of NADH, and also catalyzes the proton transfer from NADH to the quinone pool. Of these, NDHI shows high energy efficiency, and NDHII shows low energy efficiency. That is, NDHII shows a molecular number of protons that can be excreted with one electron (proton transfer value) of 0, whereas that of NDHI is considered to be 2.

In the present invention, a pathway showing a high proton transfer value per electron as described above, i.e., a respiratory chain pathway of high energy efficiency, is enhanced, and a respiratory chain pathway of low energy efficiency is made deficient. The respiratory chain pathway having high energy efficiency can be enhanced by enhancing the activity of a respiratory chain enzyme involved in the respiratory chain pathway. The respiratory chain pathway of low energy efficiency can be made deficient by reducing or eliminating the activity of a respiratory chain enzyme involved in the respiratory chain pathway.

The respiratory chain enzyme involved in a respiratory chain pathway is not particularly limited so long as it is an enzyme constituting the respiratory chain pathway. Specifically, examples thereof include dehydrogenases that catalyze electron transfer from an electron donor to a quinone pool such as ubiquinone, dimethylmenaquinone, and menaquinone, and oxidases that catalyze electron transfer from a quinone pool to an electron donor.

The oxidases that catalyze a reaction producing a water molecule by electron transfer from a quinone pool are classified as SoxM type (bo-type) and bd-type. The proton transfer value of the bo-type is 2, whereas that of the bd-type is 1. Therefore, the bo-type shows higher energy efficiency.

In the present invention, the terms "high" and "low" as used to describe energy efficiency are not absolute, but they are relative concepts, as described above.

Means for enhancing the activity of a respiratory chain enzyme of high energy efficiency, and means for reducing or eliminating activity of a respiratory chain enzyme of low energy efficiency will be explained below.

In order to enhance activity of a respiratory chain enzyme of high energy efficiency, for example, a recombinant DNA can be prepared by ligating a gene fragment coding for the enzyme to a vector which functions in the microorganism, preferably a multi-copy type vector, and introducing the ligated vector into the microorganism. The copy number of the gene coding for the enzyme in the transformed strain is thereby increased, and as a result, the enzymatic activity is amplified. This procedure will be explained below in the example section showing that the cyo operon (cyoABCDE) codes for a cytochrome bo-type oxidase, which is a respiratory chain enzyme of high energy efficiency.

The sequence of the cyo operon of *E. coli* has been reported (Chepuri et al., *The Journal of Biological Chemistry*, 265: 11185-11192 (1990)), and therefore the operon can be cloned based on the reported sequence. It is also possible to use a cyo operon derived from a bacterium belonging to the genus *Escherichia*, or derived from other organisms such as coryneform bacteria.

A plasmid autonomously replicable in *E. coli* cells can be used as a vector in gene cloning and for introduction of gene into a microorganism, for example. Specific examples thereof include pUC19, pUC18, pBR322, pHSG299, pHSG298, pHSG399, pHSG398, RSF1010, pSTV29 and so forth. A shuttle vector autonomously replicable in coryneform bacteria and *E. coli* can preferably be used for gene introduction into coryneform bacteria. Examples of plasmids autonomously replicable in coryneform bacteria are listed below pAM 330 (cf. Japanese Patent Unexamined Publication (Kokai) No. 58-67699)
pHM 1519 (cf. Japanese Patent Unexamined Publication No. 58-77895)
pAJ655 (cf. Japanese Patent Unexamined Publication No. 58-192900)
pAJ611 (cf. Japanese Patent Unexamined Publication No. 58-192900)
pAJ1844 (cf. Japanese Patent Unexamined Publication No. 58-192900)
pCG 1 (cf. Japanese Patent Unexamined Publication No. 57-134500)
pCG 2 (cf. Japanese Patent Unexamined Publication No. 58-35197)
pCG 4 (cf. Japanese Patent Unexamined Publication No. 57-183799)
pCG11 (cf. Japanese Patent Unexamined Publication No. 57-183799)
pHK4 (cf. Japanese Patent Unexamined Publication No. 5-7491)

In order to form a recombinant DNA by ligating a DNA fragment containing the cyo operon and a vector, the vector is first digested with a restriction enzyme compatible with the ends of the cyo operon. The ligation is usually performed by a ligase such as T4 DNA ligase.

To introduce the recombinant DNA prepared as described above into a microorganism, any known transformation method can be employed. For instance, a method of treating recipient cells with calcium chloride so as to increase the permeability of DNA has been reported for *E. coli* K-12 (Mandel, M. and Higa, A., *J. Mol. Biol.*, 53, 159 (1970)). Also, a method of preparing competent cells from cells at the growth phase, followed by introducing the DNA thereinto has been reported for *Bacillus subtilis* (Duncan, C. H., Wilson, G. A. and Young, F. E., *Gene*, 1, 153 (1977)). In addition to these, a method of making DNA-recipient cells into protoplasts or spheroplasts which can easily take up recombinant DNA, followed by introducing the recombinant DNA into the cells is known to be applicable to *Bacillus subtilis*, actinomycetes and yeasts (Chang, S, and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, GR., *Proc. Natl. Sci., USA*, 75, 1929 (1978)). Transformation of coryneform bacteria can be attained by the electric pulse method (see Japanese Patent Unexamined Publication No. 2-207791).

The amplification of cytochrome bo-type oxidase activity can also be attained by allowing multiple copies of the cyo operon to exist on the host's chromosomal DNA. To introduce multiple copies of the cyo operon into the chromosomal DNA of a microorganism such as bacteria belonging to the genus *Escherichia* and coryneform bacteria, homologous recombination is carried out using a sequence having multiple copies as targets on the chromosomal DNA. Repetitive DNA, or inverted repeats at the end of a transposable element can be used as sequences whose multiple copies exist in the chromosomal DNA. Also, as disclosed in Japanese Patent Unexamined Publication No. 2-109985, it is also possible to introduce multiple copies of the cyo operon into the chromosomal DNA by incorporating the cyo operon into a transposon, and transferring it. Either method will result in increasing the number of copies of the cyo operon within cells of the transformed strain, and as a result, enhancing the cytochrome bo-type oxidase activity.

Other than the aforementioned gene amplification method, enhancing the cytochrome bo-type oxidase activity can also be attained by replacing an expression regulatory sequence of cyo operon, such as a promoter, with a stronger promoter (see Japanese Patent Unexamined Publication No. 1-215280). For example, lac promoter, lip promoter, trc promoter, tac promoter, $P_R$ promoter and $P_L$, promoter of lambda phage, tet promoter, amyE promoter, and so forth are known as strong promoters. Substitution of these promoters enhances expression of the cyo operon, and hence the cytochrome bo-type oxidase activity is enhanced. The method of enhancing an expression regulatory sequence may be combined with a method of increasing the copy number of the cyo operon.

The enhancement of activity of a respiratory chain enzyme of high energy efficiency can also be attained by introducing a mutation via mutagenesis of the microorganism that results in increasing the intracellular activity of the enzyme. Examples of such a mutation include mutations of the coding region increasing the specific activity of the enzyme, mutations in the expression regulatory sequences increasing expression of the gene, and so forth. Methods utilizing treatment by ultraviolet irradiation or treatment with a known mutagenesis agent such as N-methyl-N'-nitro-N-nitrosoguanidine (NTG) and nitrous acid can be used as the mutagenesis treatment.

In order to reduce or eliminate activity of a respiratory chain enzyme of low energy efficiency, a mutation is introduced into the gene of the enzyme so that the intracellular activity of the enzyme is reduced or eliminated, or the gene on the chromosome of the microorganism is disrupted so that the gene does not function normally. The method of disrupting the ndh gene will be explained in the examples section, which shows ndh coding for NDH-II as a gene of a respiratory chain enzyme of low energy efficiency.

The sequence of ndh of *E. coli* has been reported (Young et al., *European Journal of Biochemistry*, 116:165-170 (1981)), and therefore the gene can be cloned based on the reported sequence. It is also possible to use a ndh gene derived from a bacterium belonging to the genus *Escherichia*, or derived from other organisms such as coryneform bacteria.

A ndh gene on the chromosome can be disrupted by transforming a microorganism with DNA containing a ndh gene modified with an internal deletion so as to not produce a functional NDH-II (deletion-type ndh gene), and allowing recombination between the deletion-type ndh gene and the ndh gene on the chromosome. Gene destruction by homologous recombination has already been established, and there are methods utilizing a linear DNA, a plasmid that contains a temperature-sensitive replication control region, and so forth. In the present invention, the method utilizing a plasmid that contains a temperature-sensitive replication control region is preferred.

A ndh gene on the host chromosome can be replaced with the deletion-type ndh gene as follows. A microorganism is transformed with a recombinant DNA prepared by inserting a temperature-sensitive replication control region, deletion-type ndh gene, and marker gene for resistance to a drug. Furthermore, the resulting transformed strain is cultured at a temperature at which the temperature-sensitive replication control region does not function, and then the transformed strain can be cultured in a medium containing the drug, which results in obtaining a transformed strain in which the recombinant DNA is incorporated into the chromosomal DNA.

In the transformed strain having the recombinant DNA incorporated into the chromosomal DNA as described above, the deletion-type ndh gene is recombined with the ndh gene originally present on the chromosome, and the two fusion chromosomal ndh-deletion-type ndh genes are inserted into the chromosome so that the other portions of the recombinant DNA (vector segment, temperature-sensitive replication control region and drug resistance marker) are present between the two fusion genes. Therefore, the transformant expresses NDH-II, because the normal ndh gene is dominant in this state.

Then, in order to leave only the deletion-type ndh gene on the chromosomal DNA, one copy of the ndh gene is eliminated together with the vector segment (including the temperature-sensitive replication control region and the drug resistance marker) from the chromosomal DNA by recombination of the two ndh genes. In that case, the normal ndh gene is left on the chromosomal DNA, and the deletion-type ndh gene is excised from the chromosomal DNA. To the contrary, the deletion-type ndh gene can be left on the chromosomal DNA, and the normal ndh gene can be excised from the chromosome DNA. In the both cases, the excised DNA may be retained in the cell as a plasmid when the cell is cultured at a temperature at which the temperature-sensitive replication control region can function. Subsequently, the cell is cultured at a temperature at which the temperature-sensitive replication control region cannot function, resulting indropping out the plasmid DNA, and ndh gene deletion mutant can be obtained.

Examples of the vector having a temperature-sensitive replication origin for *E. coli* include, for example, the plasmid pMAN997 described in International Patent Publication WO99/03988, and so forth. Examples of the vector having a temperature-sensitive replication origin for coryneform bacteria include, for example, the plasmid pHSC4 disclosed in Japanese Patent Unexamined Publication No. 5-7491, and so forth. However, the plasmids are not limited to these, and other vectors can also be used.

Specific examples of a microorganism obtained as described above include microorganisms wherein one or both of SoxM type oxidase or NDH-1 is enhanced, microorganisms wherein the activities of one or both of cytochrome bd-type oxidase or NDH-II are reduced or eliminated, and microorganism wherein one or both of SoxM type oxidase or NDH-1 are enhanced, and wherein activities of one or both of cytochrome bd type oxidase or NDH-II are reduced or eliminated. More specifically, there can be mentioned, for example, *E. coli* wherein the activity of SoxM type oxidase is enhanced and the activity of NDH-II is made deficient. Examples of SoxM type oxidase include cytochrome bo-type oxidase.

The microorganism used for the present invention is not particularly limited so long as it can be imparted with the aforementioned properties, and examples thereof include bacteria belonging to the genus *Escherichia* such as *E. coli*, coryneform bacteria such as *Brevibacterium lactofermentum* (*Corynebacterium glutamicum*), *Bacillus* bacteria such as *Bacillus subtilis, Serratia* bacteria such as *Serratia marcescens*, yeast such as *Saccharomyces cerevisae*, and so forth.

Specifically, there can be mentioned, when the fermentation product is L-threonine, *E. coli* VKPM B-3996 (RIA 1867) (refer to U.S. Pat. No. 5,175,107), *Corynebacterium acetoacidophilum* AJ12318 (FIRM BP-1172) (refer to U.S. Pat. No. 5,188,949), and so forth; for L-lysine, there can be mentioned *E. coli* AJ11442 (NRRL B-12185, FERM BP-1543) (refer to U.S. Pat. No. 4,346,170), *E. coli* W3110 (tyrA) (this strain is obtained by eliminating plasmid pHATerm from *E. coli* W3110 (tyrA)/pHATerm (FERM BP-3653), refer to International Patent Publication WO95/16042), *Brevibacterium lactofermentum* AJ12435 (FERM BP-2294) (U.S. Pat. No. 5,304,476), *Brevibacterium lactofermentum* AJ3990 (ATCC31269) (refer to U.S. Pat. No. 4,066,501) etc.; for L-glutamic acid, there can be mentioned *E. coli* AJ12624 (FERM BP-3853) (refer to the French Patent Unexamined Publication No. 2,680,178), *Brevibacterium lactofermentum* AJ12821 (FERM BP-4172) (Japanese Patent Unexamined Publication No. 5-26811, French Patent Unexamined Publication No. 2,701,489), *Brevibacterium lactofermentum* AJ12475 (FERM BP-2922) (refer to U.S. Pat. No. 5,272, 067), *Brevibacterium lactofermentum* AJ13029 (FERM BP-5189) (refer to International Patent Application JP95/ 01586) etc.; for L-leucine, there can be mentioned *E. coli* AJ11478 (FERM P-5274) (refer to Japanese Patent Publication (Kokoku) No. 62-34397), *Brevibacterium lactofermentum* AJ3718 (FERM P-2516) (refer to U.S. Pat. No. 3,970, 519) etc.; for L-isoleucine, there can be mentioned *E. coli* KX141 (VKPM B-4781) (refer to the European Patent Unexamined Publication No. 519,113), *Brevibacterium flavum* AJ12149 (FERM BP-759) (refer to U.S. Pat. No. 4,656,135) etc.; for L-valine, there can be mentioned *E. coli* VL1970 (VKPM B-4411) (refer to European Patent Unexamined Publication No. 519,113), *Brevibacterium lactofermentum* AJ12341 (FERM BP-1763) (refer to U.S. Pat. No. 5,188,948) etc.; for L-phenylalanine, there can be mentioned *E. coli* AJ12604 (FERM BP-3579) (Japanese Patent Unexamined Publication No. 5-236947, European Patent Unexamined Publication No. 488,424), *Brevibacterium lactofermentum* AJ12637 ERM BP-4160) (refer to the French Patent Unexamined Publication No. 2,686,898), and so forth.

In the microorganism used for the present invention, the activity of an enzyme involved in biosynthesis of the target substance may be enhanced, depending on the target substance. Furthermore, the activity of an enzyme disadvantageous for the production of the target substance may be reduced or eliminated.

A target substance can be produced by culturing such a microorganism as described above in a medium to produce and cause accumulation of the target substance in the medium, and collecting the target substance.

The medium used for the production of a target substance may be a conventionally used well-known medium and can be selected depending on the microorganism to be utilized. That is, the medium may be a usual medium containing a carbon source, nitrogen source, inorganic ions, as well as other organic components, if necessary. A special medium is not required for practicing the present invention.

As the carbon source, it is possible to use sugars such as glucose, lactose, galactose, fructose or starch hydrolysate; alcohols such as glycerol or sorbitol; organic acids such as fumaric acid, citric acid or succinic acid, and so forth.

As the nitrogen source, it is possible to use inorganic ammonium salts such as ammonium sulfate, ammonium chloride or ammonium phosphate; organic nitrogen such as soybean hydrolysate; ammonia gas; aqueous ammonia, and so forth.

It is desirable for the medium to contain required substances such as vitamin $B_1$, L-homoserine, and L-tyrosine, or yeast extract in appropriate amounts as organic trace nutrients. Other than the above, potassium phosphate, magnesium sulfate, iron ion, manganese ion, and so forth are added in small amounts, if necessary.

The culture can be performed under conventional well-known conditions and can be selected according to a microorganism to be utilized. For example, the culture is preferably performed under aerobic conditions for 16-120 hours. The culture temperature is preferably maintained at 25° C. to 45° C., and pH is preferably maintained at 5-8 during the culture. Inorganic or organic, acidic or alkaline substances as well as ammonia gas, or the like can be used for pH adjustment.

For collection of the metabolic product from the medium after the culture, special methods are not required for the present invention. That is, the present invention can be practiced by using a combination of conventional well-known ion exchange techniques, precipitation techniques and other techniques.

BEST MODE FOR CARRYING OUT THE INVENTION

Hereafter, the present invention will be explained more specifically with reference to the following examples.

Example 1

Cloning of Cytochrome Bo-Type Oxidase Gene

The sequence of the cyo operon (cyoABCDE) coding for the cytochrome bo-type oxidase of *E. coli* had been already reported (Chepuri et al., *The Journal of Biological Chemistry*, 265:11185-11192 (1990)), and therefore the operon was cloned based on the sequence.

Specifically, the target cyo operon gene was obtained from the phage library of Kohara (Kohara et al., *Cell*, 50:495-508 (1987)) containing the cyo operon. Phage DNA was obtained from the phage clone 147[2H5] of Kohara containing the operon using Wizard lambda prep (Promega). The obtained phage DNA 147[2H5] was digested with PshBI, and the obtained 5.5 kb fragment containing the cyo operon was blunt-ended, and inserted into the SmaI site of pMW119 (Nippon Gene) to clone the cyo operon containing a promoter region. In the obtained plasmid, the cyo operon was inserted in the reverse direction with respect to the lactose operon promoter on pMW119. This plasmid was designated pMW(CYO)B.

The plasmid pMW(CYO)B was introduced into *E. coli* W3110 strain (obtained from the National Institute of Genetics, Mishima, Shizuoka, Japan) to obtain W3110/pMW(CYO)B. Ubiquinol oxidase activity present in the cell extracts of W3110 and W3110/pMW(CYO)B strains was measured as terminal oxidase activity by using a known method (Kita et al., *The Journal of Biological Chemistry*, 259:3368-3374 (1984)). The results are shown in Table 1.

TABLE 1

| Ubiquinol oxidase activity | |
|---|---|
| Strain | Ubiquinol oxidase activity (mmol/min/mg protein) |
| W3110/pMW119 | 0.28 |
| W3110/pMW(CYO)B | 0.56 |

It was found that the terminal oxidase activity was enhanced in the strain introduced with pMW(CYO)B as shown in Table 1. This enhancement of the terminal oxidase activity is considered to be caused by the enhancement of cytochrome bo-type oxidase activity through the enhancement of cyo operon.

Example 2

Acquisition of NDH-II Deficient Strain

In order to produce a NDH-II deficient strain, an internally cleaved partial sequence of NDH-II (disrupted type NDH-II gene) was prepared. The partial sequence of NDH-II was cloned based on the known sequence of the gene ndh coding for NDH-II of *E. coli* (Young et al., *European Journal of Biochemistry*, 116:165-170 (1981)).

Figure 1:
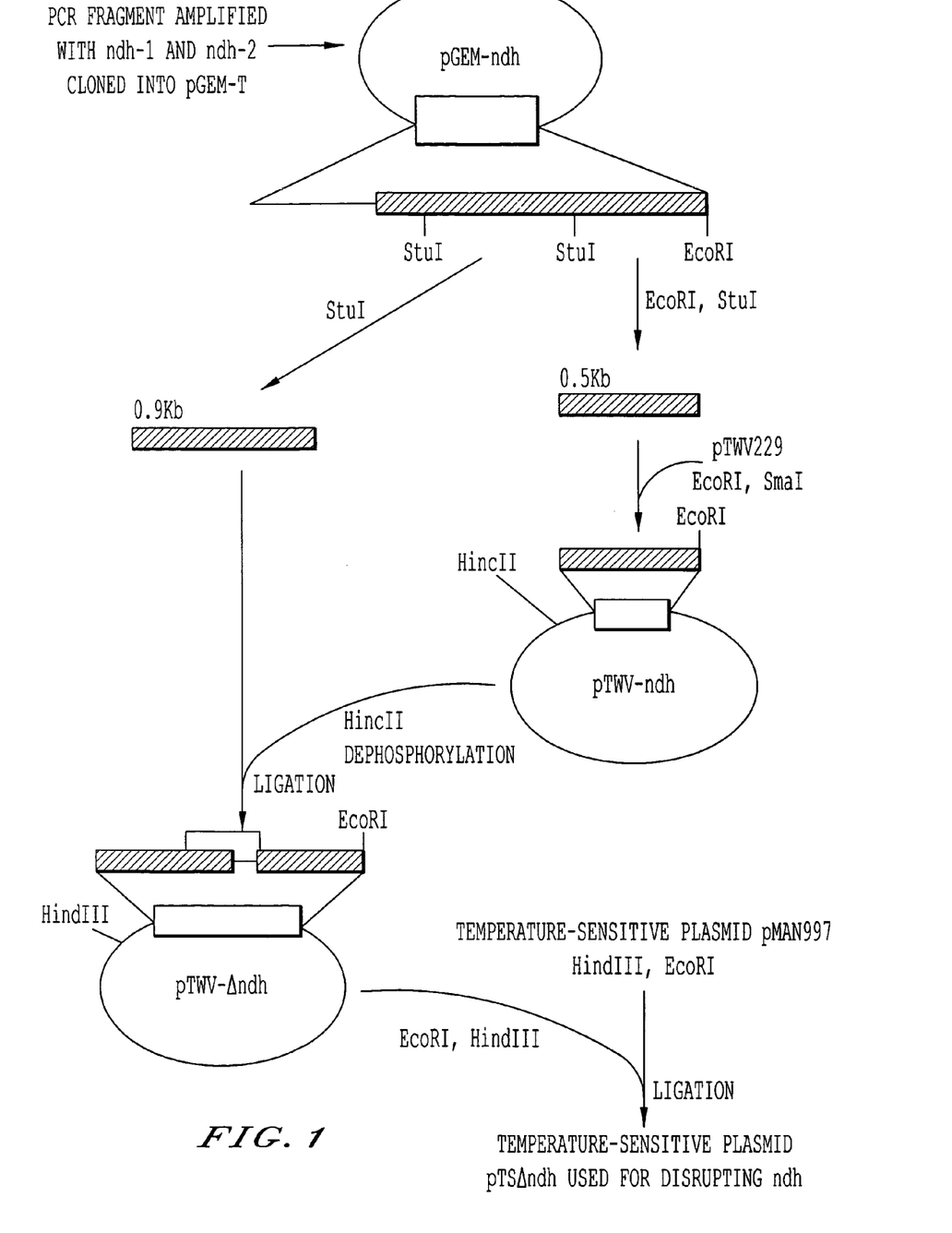
FIG. 1 shows construction of plasmid pTS-Δndh for producing NDH-II gene-disrupted strain.

Specifically, the disrupted type NDH-II gene was produced as follows (FIG. 1). First, a DNA fragment of about 2.4 kb containing the partial sequence of NDH-II was amplified from *E. coli* chromosomal DNA by PCR using ndh-1 (SEQ ID NO: 1) and ndh-2 (SEQ ID NO: 2) as primers. This fragment was cloned into pGEM-T vector (Promega) to obtain pGEM-ndh. This pGEM-ndh was digested with restriction enzymes EcoRI and StuI, and the obtained DNA fragment of 0.5 kb was collected and ligated to pTWV229 (Takara Shuzo), which had been digested with EcoRI and SmaI, to obtain pTWV-ndh.

Then, pGEM-ndh was digested with a restriction enzyme StuI, and the obtained DNA fragment of 0.9 kb was collected and inserted into the HincII site of pTWV-ndh. Thus, pTWVΔndh was obtained containing a part of the multi-cloning sites of pTWV229 in the partial sequence of ndh. The plasmid pTWVΔndh contained the ndh sequence inserted with a sequence of 17 bp derived from pTWV229 at the StuI site in the ndh sequence. Subsequently, a fragment of 1.5 kb obtained by digesting pTWVΔndh with HindIII and EcoRI was inserted between the HindIII and EcoRI sites of the temperature-sensitive plasmid pMAN997 (refer to International Patent Publication WO 99/03988) to obtain pTS-Δndh. Homologous recombination was performed between this plasmid pTS-Δndh and the genome of W3110 strain as for ndh by a usual homologous recombination technique utilizing the temperature sensitivity of pTS-Δndh (Matuyama et al., *Journal of Bacteriology*, 162:1196 (1985)) to obtain a W3110(ndh) strain that did not express normal NDH-II protein because the sequence of 17 bp derived from pTWV229 was inserted in the coding region of ndh on the genome. From W3110(tyrA), tyrA deficiency was introduced into the W3110(ndh) strain by P1 transduction using tetracycline resistance as a marker to obtain a W3110(ndh, tyrA) strain.

Figure 2:
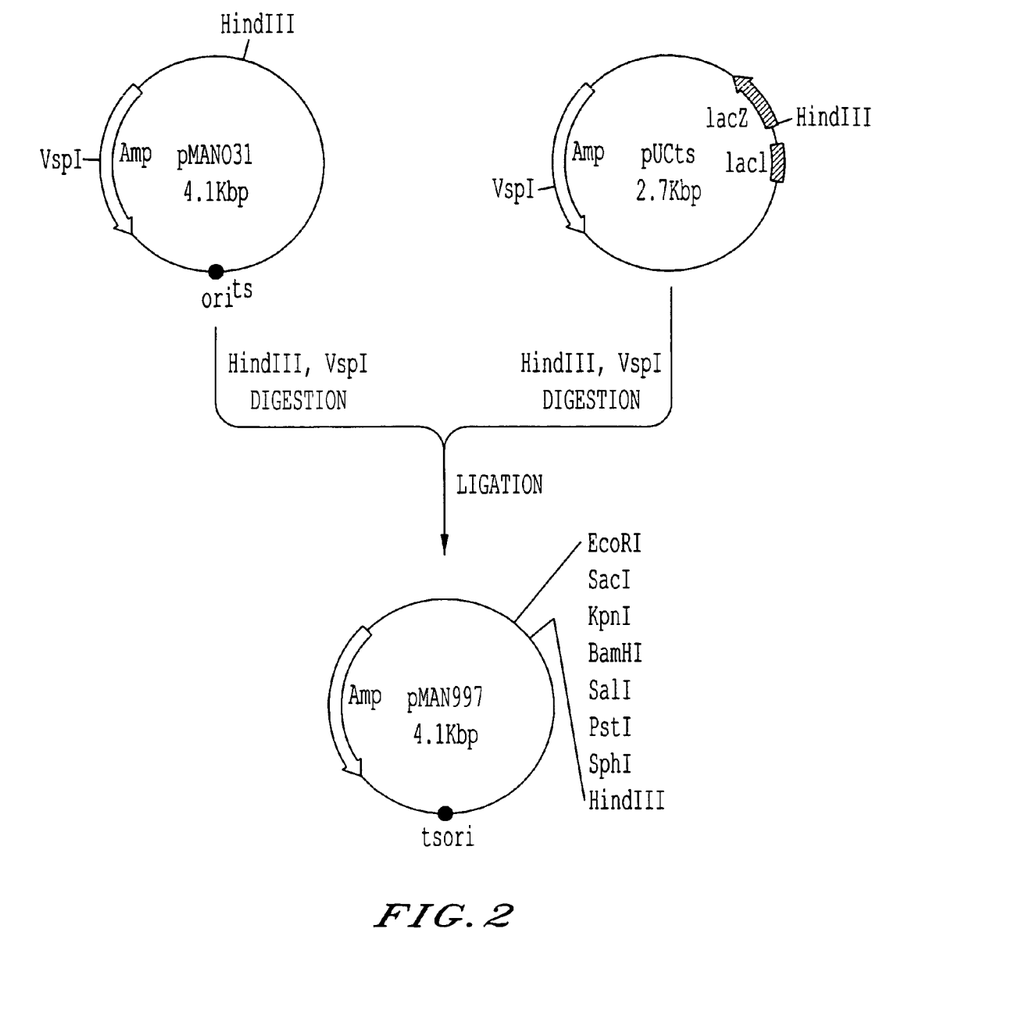
FIG. 2 shows construction of pMAN997.

The aforementioned pMAN997 was obtained by exchanging the VspI-HindIII fragments of pMAN031 (*J. Bacteriol*, 162, 1196 (1985)) and pUC19 (Takara Shuzo) (FIG. 2).

Furthermore, while the W3110(tyrA) strain is detailed in European Patent Unexamined Publication No. 488424/1992, its preparation method will be briefly explained below.

The *E. coli* W3110 strain was obtained from the National Institute of Genetics (Mishima, Shizuoka). This strain was seeded on an LB plate containing streptomycin, and a strain that formed a colony was selected to obtain a streptomycin-resistant strain. The selected streptomycin resistant strain and *E. coli* K-12 ME8424 strain were mixed, and cultured in a complete medium (L-Broth: 1% Bacto trypton, 0.5% Yeast extract, 0.5% NaCl) at 37° C. for 15 minutes as stationary culture to induce conjugation. The *E. coli* K-12 ME8424 strain has the genetic traits of (HfrPO45, thi, relA1, tyrA:: Tn10, ung-1, nadB), and it can be obtained from the National Institute of Genetics. Thereafter, the culture was seeded in a complete medium (L-Broth: 1% Bacto trypton, 0.5% Yeast extract, 0.5% NaCl, 1.5% agar) containing streptomycin, tetracycline and L-tyrosine, and a strain that formed a colony was selected. This strain was designated as *E. coli* W3110 (tyrA) strain.

European Patent Unexamined Publication No. 488424/1992 discloses many strains obtained by introducing a plasmid into the above strain. For example, a strain obtained by introducing a plasmid pHATerm was designated as *E. coli* W3110(tyrA)/pHATerm, deposited on Nov. 16, 1991, at the National Institute of Bioscience and Human-Technology, Agency of Industrial Science and Technology, Ministry of International Trade and Industry (1-3 Higashi 1-Chome, Tsukuba-shi, Ibaraki-ken, Japan, postal code: 305) (currently, the independent administrative corporation, the National Institute of Advanced Industrial Science and Technology, International Patent Organism Depositary (Chuo Dai-6, 1-1 Higashi 1-Chome, Tsukuba-shi, Ibaraki-ken, Japan, postal code: 305-5466) as an international deposition under the provisions of the Budapest Treaty, and received an accession number of FERM BP-3653. The *E. coli* W3110(tyrA) strain can be obtained by eliminating the plasmid pHATerm from the above strain in a conventional manner.

Example 3

Production of L-Lysine

The plasmid pMW(CYO)B obtained in Example 1 was introduced into the W3110(tyrA) strain and the W3110(ndh, tyrA) strain obtained in Example 2 to obtain W3110(tyrA)/pMW(CYO)B and W3110(ndh, tyrA)/pMW(CYO)B, respectively. Similarly, pMW119 was introduced into W3110 (tyrA) to obtain W3110(tyrA)/pMW119 strain. L-lysine production by these W3110(tyrA)/pMW(CYO)B strain, W3110 (ndh, tyrA)/pMW(CYO)B strain, and W3110(tyrA)/pMW119 as a control was evaluated by culture in flask. The culture was performed by using a medium having the following composition at 37° C. for 24 to 48 hours with shaking. The results are shown in Table 2.

| (Medium composition) | |
|---|---|
| Glucose | 40 g/L |
| $MgSO_4.7H_2O$ | 1 g/L |
| $KH_2PO_4$ | 1 g/L |
| $FeSO_4.7H_2O$ | 0.01 g/L |
| $MnSO_4.5H_2O$ | 0.01 g/L |
| Yeast Extract (Difco) | 2 g/L |
| L-Tyrosine | 0.1 g/L or 0.05 g/L |

The medium was adjusted to pH 7.0 with KOH, and autoclaved at 115° C. for 10 minutes. However, glucose and $MgSO_4.7H_2O$ were sterilized separately. Further, before the culture, 30 g/L of $CaCO_3$ (Japanese Pharmacopoeia), which was subjected to dry sterilization at 180° C., and 100 μg/L of an antibiotics, ampicillin, were added to the medium.

TABLE 2

L-lysine production amount

| Strain | L-Lys (g/L) |
|---|---|
| W3110(tyrA)/pMW119 | 0.29 |
| W3110(tyrA)/pMW(CYO)B | 0.48 |
| W3110(ndh, tyrA)/pMW(CYO) | 0.53 |

It was found that the L-lysine productivity was improved in the *E. coli* producing L-lysine by enhancing the cytochrome bo-type oxidase activity. This is considered to be caused because energy acquisition efficiency was improved by enhancement of the respiratory chain pathway of high energy efficiency, and the energy was used for the L-lysine production.

It was also found that the L-lysine productivity was improved in the *E. coli* producing L-lysine by making NDH-II deficient. This is considered to be caused because energy acquisition efficiency was improved by deficiency of the respiratory chain pathway of low energy efficiency, and the energy was used for the L-lysine production.

Example 4

Production L-Threonine

The plasmid pMW(CYO)B obtained by the aforementioned method was introduced into an L-threonine producing bacterium, *E. coli* VKPM B-3996 (RIA 1867) (refer to U.S. Pat. No. 5,175,107, hereafter referred to as "B-3996" strain) to obtain B-3996/pMW(CYO)B strain. The B-3996 strain harbored a plasmid pVIC40 (International Patent Publication WO90/04636) obtained by inserting the threonine operon into a wide host-range vector plasmid pAYC32 containing a streptomycin resistance marker (refer to Chistorerdov, A. Y., Tsygankov, Y. D., *Plasmid*, 1986, 16, 161-167). The B-3996 strain was deposited at USSR Antibiotics Research Institute (VNIIA) under a registration number of RIA1867.

As a control, B-3996/pMW119 was obtained by introducing pMW119 into B-3996. The L-threonine productivity of these B-3996/pMW(CYO)B and B-3996/pMW119 was evaluated by culture in flask. The culture was performed by using a medium having the composition mentioned in Table 3 at a temperature of 37° C. for 38 hours with stirring at 114-116 rpm. Component A, Component B and Component C mentioned in Table 3 were prepared and sterilized separately, and then they were cooled and mixed in a ratio of 16/20 volume of Component A, 4/20 volume of Component B and 30 g/L, of Component C. The results are shown in Table 4.

TABLE 3

Threonine production medium

| A | $(NH_4)_2SO_4$ | 16 g/L |
|---|---|---|
| | $KH_2PO_4$ | 1 g/L |
| | $FeSO_4.7H_2O$ | 0.01 g/L |
| | $MnSO_4.4H_2O$ | 0.01 g/L |
| | Yeast Extract (Difco) | 2 g/L |
| | L-Isoleucine | 50 mg/L |
| | Nicotinic acid | 10 mg/L |
| | Adjusted to pH 7.0 with KOH and autoclaved at 115° C. for 10 minute (16/20 volume) | |
| B | 20% glucose autoclaved at 115° C. for 10 minute (4/20 volume) | |
| | $MgSO_4.7H_2O$ | 1 g/L |
| C | $CaCO_3$ according to Japanese Pharmacopoeia, subjected to dry sterilization at 180° C. (30 g/L) | |
| | Antibiotics (100 μg/L of streptomycin and 5 μg/L of kanamycin) | |

TABLE 4

Production amount of L-threonine

| Strain | L-Thr (g/L) |
|---|---|
| B-3996/pMW119 | 13.1 |
| B-3996/pMW(CYO)B | 14.3 |

It was found that the L-threonine productivity of L-threonine-producing *E. coli* could be improved by enhancing cytochrome bo-type oxidase activity.

Example 5

Production of L-Phenylalanine

A plasmid pACMAB was collected from the *E. coli* W3110 (tyrA)/pACMAB, pBR-aroG4 strain according to a usual purification method for a plasmid. The plasmid was obtained by inserting a DNA fragment containing a gene for desensitized-type chorismate mutase/prephenate dehydratase (CM-PDH) in the proper L-phenylalanine biosynthesis system between the BamHI and HindIII cleavage sites of the plasmid vector pACYC184 (Ap$^r$) (refer to International Patent Publication WO97/08333). The W3110(tyrA)/pACMAB, pBR-aroG4 strain (designated as AJ12604) was deposited on Jan. 28, 1991 at the National Institute of Bioscience and Human-Technology, Agency of Industrial Science and Technology, Ministry of International Trade and Industry (1-3 Higashi 1-Chome, Tsukuba-shi, Ibaraki-ken, Japan, postal code: 305) and received an accession number of FERM P-11975. Then, it was converted to an international deposit under the provisions of the Budapest Treaty on Sep. 26, 1991, and received an accession number of FERM BP-3579.

The plasmid pACMAB was blunt-ended by digestion with SalI. Into this, a blunt-ended DNA fragment containing the cyo operon of 5.5 kb, which was obtained from the aforementioned phage DNA 147[2H5] of Kohara by digestion with PshBI, was inserted. The obtained plasmid pACMAB-cyo was introduced into W3110(tyrA/pBR-aroG4). The obtained transformant strain was cultured in a medium for L-phenylalanine production (containing 20 g of glucose, 29.4 g of disodium hydrogenphosphate, 6 g of potassium dihydrogenphosphate, 1 g sodium chloride, 2 g of ammonium chloride, 10 g of sodium citrate, 0.4 g of sodium glutamate, 3 g of magnesium sulfate heptahydrate, 0.23 g of calcium chloride, 2 mg of thiamin hydrochloride, and 100 mg of L-tyrosine in 1 L of water, pH 7.0) at 37° C. for 40 hours. L-Phenylalanine contained in the medium was quantified by high performance liquid chromatography. The results are shown in Table 5.

TABLE 5

Production amount of L-phenylalanine

| Strain | L-Phe (g/L) |
|---|---|
| W3110(tyrA)/pACMAB, pBR-aroG4 | 3.9 |
| W3110(tyrA)/pACMAB-cyo, pBR-aroG4 | 4.2 |

It was found that the L-phenylalanine productivity of the L-phenylalanine producing *E. coli* was improved by enhancing the cytochrome bo-type oxidase activity.

---

---

What is claimed is:

1. A method for producing an L-amino acid, comprising:
   A) culturing an *Escherichia coli* in a medium to produce and accumulate the L-amino acid in the medium; and
   B) collecting said L-amino acid from said medium,
   wherein the *Escherichia coli* has been modified so to have enhanced activity of cytochrome bo-type oxidase in comparison to an unmodified *Escherichia coli* by a method selected from the group consisting of
   i) increasing the copy number of a gene coding for said oxidase,
   ii) modifying an expression regulatory sequence of said gene, and
   iii) combinations thereof.

2. The method according to claim 1, wherein said L-amino acid is L-lysine.

3. The method according to claim 1, wherein said L-amino acid is L-threonine.

4. The method according to claim 1, wherein said L-amino acid is L-phenylalanine.

5. The method according to claim 1, wherein said cytochrome bo type oxidase is encoded by cyo operon.

6. The method according to claim 1, wherein said expression regulatory sequence is a promoter.

* * * * *